United States Patent [19]
Jensen

[11] Patent Number: 6,106,511
[45] Date of Patent: *Aug. 22, 2000

[54] METHODS AND DEVICES FOR POSITIONING A SURGICAL INSTRUMENT AT A SURGICAL SITE

[75] Inventor: Joel F. Jensen, Redwood City, Calif.

[73] Assignee: SRI International, Menlo Park, Calif.

[*] Notice: This patent is subject to a terminal disclaimer.

[21] Appl. No.: 09/149,828

[22] Filed: Sep. 8, 1998

Related U.S. Application Data

[60] Continuation of application No. 08/504,620, Jul. 20, 1995, Pat. No. 5,817,084, which is a division of application No. 08/062,404, May 14, 1993, abandoned.

[51] Int. Cl.$^7$ ..................................................... A61B 17/00
[52] U.S. Cl. ........................... 606/1; 606/130; 600/102; 600/104
[58] Field of Search ........................... 606/1, 130; 414/1, 414/917; 901/16, 27, 31, 32, 41; 128/897, 898; 600/137, 104, 102, 106, 201, 204, 218, 219, 225

[56] References Cited

U.S. PATENT DOCUMENTS

| | | |
|---|---|---|
| 2,815,697 | 12/1957 | Saunders-Singer . |
| 3,463,329 | 8/1969 | Gartner . |
| 4,260,319 | 4/1981 | Motoda et al. . |
| 4,543,033 | 9/1985 | Czermak et al. . |

(List continued on next page.)

FOREIGN PATENT DOCUMENTS

| | | |
|---|---|---|
| 239 409 | 9/1987 | European Pat. Off. . |
| 291 292 | 11/1988 | European Pat. Off. . |
| 595 291 | 5/1994 | European Pat. Off. . |
| 2 460 762 | 1/1981 | France . |
| 2 593 106 | 7/1987 | France . |
| 28 19 976 | 11/1979 | Germany . |
| 0482439 | 1/1970 | Switzerland . |
| 2117732 | 10/1983 | United Kingdom . |
| WO 95/01757 | 1/1995 | WIPO . |

OTHER PUBLICATIONS

Guerrouad, Aicha et al., "S.M.O.S.: Stereotaxical Microtele- manipulator for Ocular Surgery," *IEEE Engineering in Medicine & Biology Society 11$^{th}$ Annual Int'l Conf.*, 1989, pp. 879–880.

Gayed, Ben, "An Advanced Control Micromanipulator for Surgical Applications," *Systems Science*, 1987, vol. 13, pp. 123–133.

Ng, W.S. et al., "Robotic Surgery," *IEEE Engineering in Medicine and Biology*, Mar. 1993, pp. 120–125.

Alexander, III, Arthur D., "Impacts of Telemation on Modern Society," *International Centre for Mechanical Sciences, First CISM—IFToMM Symposium on Robots and Manipulators*, vol. II, pp. 121–136 (Sep. 5–8, 1973).

*Primary Examiner*—Linda C. M. Dvorak
*Assistant Examiner*—Bryan K. Yarnell
*Attorney, Agent, or Firm*—Townsend and Townsend and Crew

[57] ABSTRACT

For positioning a surgical instrument at a surgical site, an elongate tubular structure is coupled to the distal portion of a robotic arm. This structure is adapted to be inserted in the body cavity of a patient and is adapted to receive the surgical instrument and serve as a guide for the surgical instrument into the patient's body. The robotic arm may have a parallelogram center of motion linkage and actuators for driving various degrees of freedom of movement of the arm and the surgical instrument. The robotic arm may be remotely controlled by an operator manipulating an input device.

32 Claims, 7 Drawing Sheets

U.S. PATENT DOCUMENTS

| | | |
|---|---|---|
| 4,696,501 | 9/1987 | Webb . |
| 4,897,015 | 1/1990 | Abbe et al. . |
| 4,921,393 | 5/1990 | Andeen et al. . |
| 5,060,532 | 10/1991 | Barker . |
| 5,078,140 | 1/1992 | Kwoh . |
| 5,129,911 | 7/1992 | Siczek et al. . |
| 5,184,601 | 2/1993 | Putman . |
| 5,209,747 | 5/1993 | Knoepfler . |
| 5,219,351 | 6/1993 | Teubner et al. . |
| 5,222,409 | 6/1993 | Dalakian . |
| 5,257,998 | 11/1993 | Ota et al. . |
| 5,273,039 | 12/1993 | Fujiwara et al. . |
| 5,279,309 | 1/1994 | Taylor et al. . |
| 5,343,385 | 8/1994 | Joskowicz et al. ............... 364/167.01 |
| 5,368,015 | 11/1994 | Wilk . |
| 5,397,323 | 3/1995 | Taylor et al. . |
| 5,402,801 | 4/1995 | Taylor . |
| 5,417,210 | 5/1995 | Funda et al. . |
| 5,445,166 | 8/1995 | Taylor ........................ 128/897 |
| 5,572,999 | 11/1996 | Funda et al. . |
| 5,630,431 | 5/1997 | Taylor . |
| 5,695,500 | 12/1997 | Taylor et al. .................. 606/130 |
| 5,697,939 | 12/1997 | Kubota et al. ................. 606/130 |
| 5,749,362 | 5/1998 | Funda et al. . |
| 5,762,458 | 6/1998 | Wang et al. .................... 414/1 |
| 5,800,423 | 9/1998 | Jensen ........................ 606/1 |
| 5,808,665 | 9/1998 | Green ........................ 348/65 |
| 5,815,640 | 9/1998 | Wang et al. .................... 395/86 |
| 5,817,084 | 10/1998 | Jensen ........................ 606/1 |
| 5,841,950 | 11/1998 | Wang et al. .................... 395/99 |
| 5,855,583 | 1/1999 | Wang et al. .................... 606/139 |
| 5,876,325 | 3/1999 | Mizuno et al. ................ 600/102 |
| 5,878,193 | 3/1999 | Wang et al. .................... 395/86 |
| 5,907,664 | 5/1999 | Wang et al. .................... 395/86 |
| 5,931,832 | 8/1999 | Jensen ........................ 606/1 |
| 6,001,108 | 12/1999 | Wang et al. .................... 606/130 |
| 6,007,550 | 12/1999 | Wang et al. .................... 606/139 |

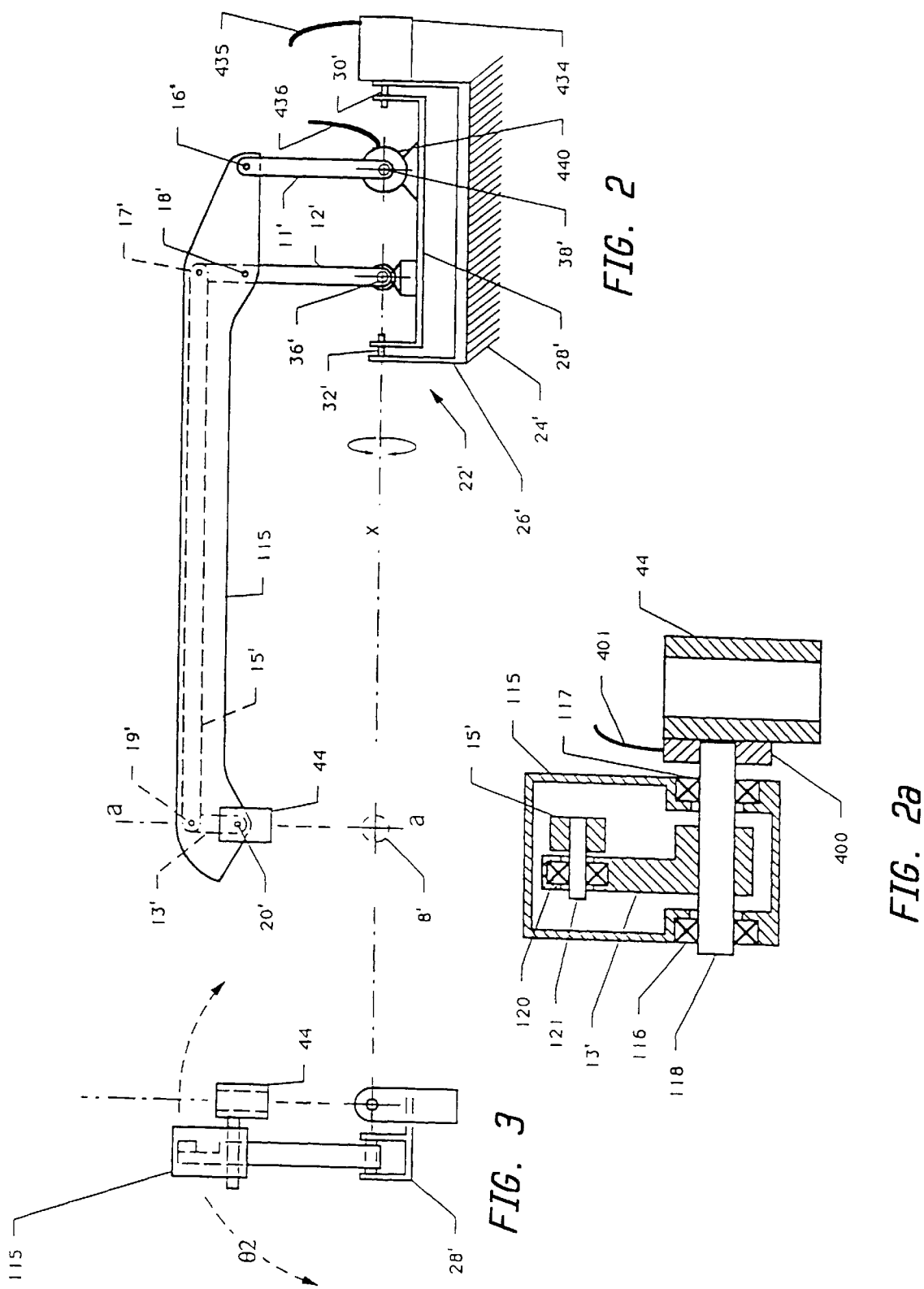

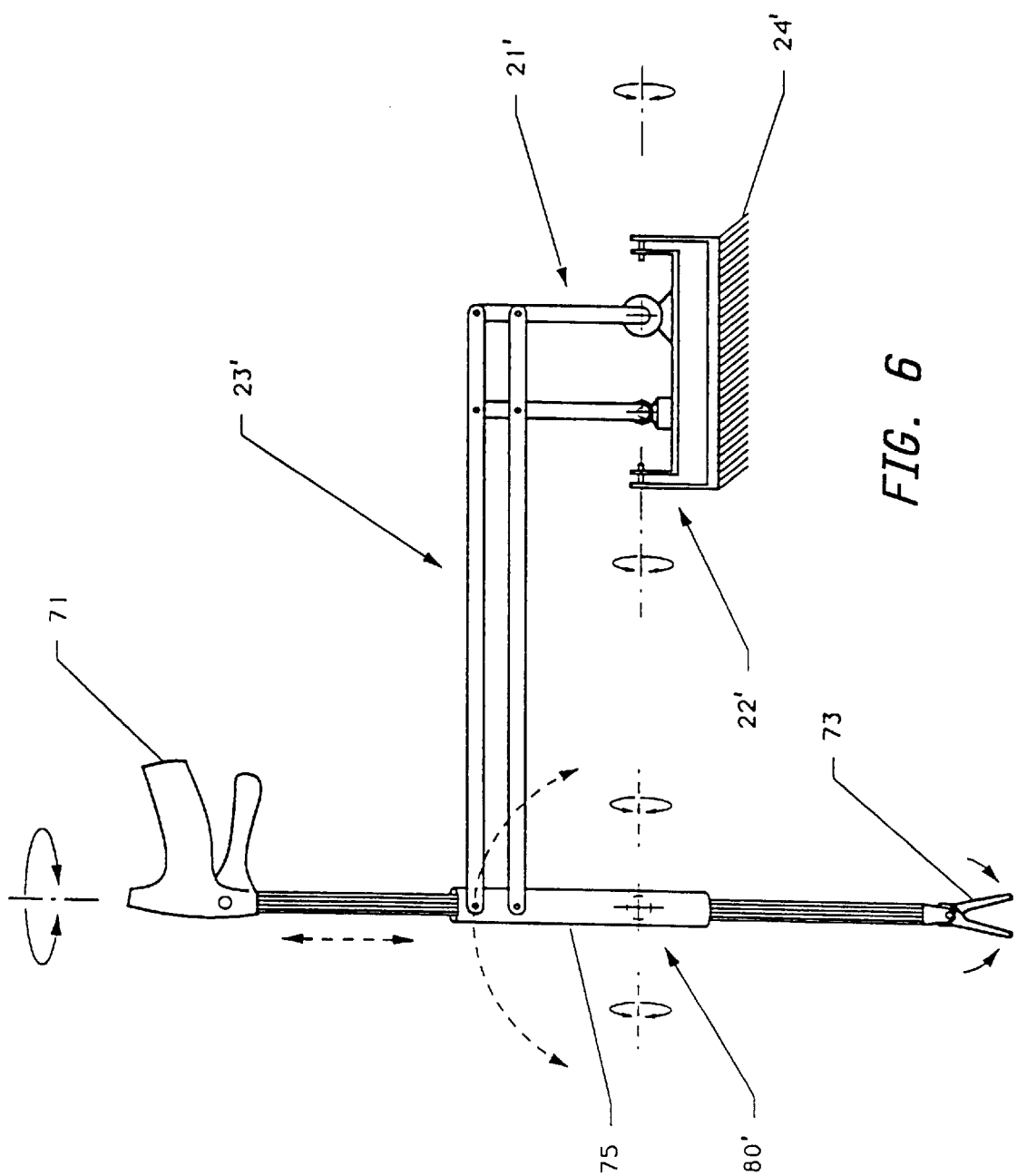

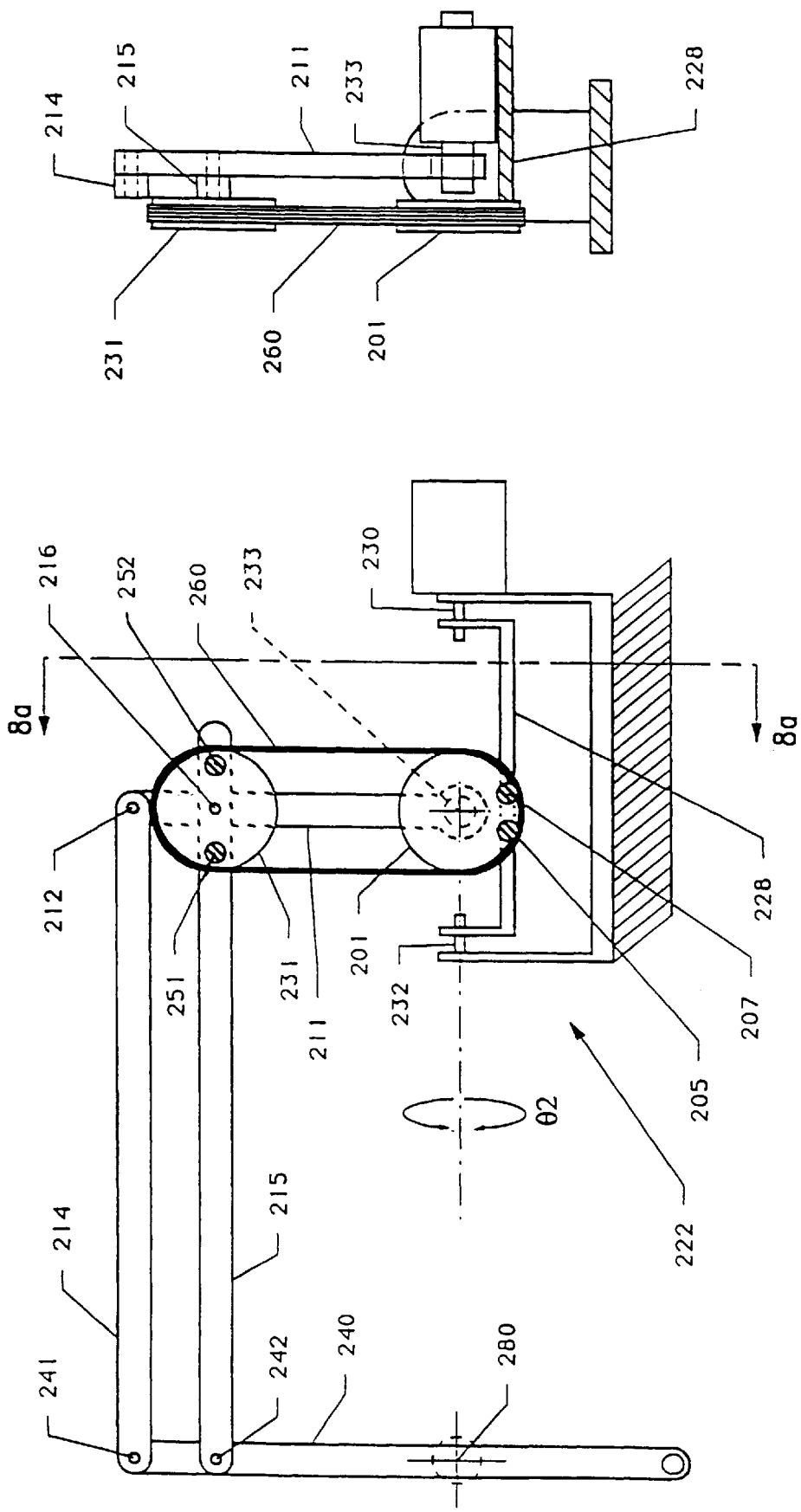

METHODS AND DEVICES FOR POSITIONING A SURGICAL INSTRUMENT AT A SURGICAL SITE

This U.S. patent application is a continuation of application U.S. Ser. No. 08/504,620, filed Jul. 20, 1995, now U.S. Pat. No. 5,817,084, which is a divisional of application U.S. Ser. No. 08/062,404, filed May 5, 1993 now abandoned, the full disclosures of which are incorporated herein by reference.

BACKGROUND OF THE INVENTION

The present invention is directed to a remote center positioner used to support an instrument and provide a center of spherical rotation, remote from any bearings or mechanical supports, at a desired location of the instrument. Specifically, the remote center positioner is useful in laparoscopic surgery to constrain a surgical instrument to move around a fixed center of rotation remote from any bearings or mechanical supports and coincident with an entry incision in the patient's abdominal wall.

In standard laparoscopic abdominal surgery, the patient's abdomen is insufflated with gas, and cannulas are passed through small (approximately ½ inch) incisions to provide entry ports for laparoscopic surgical instruments. The laparoscopic surgical instruments generally include an laparoscope for viewing the surgical field, and working tools such as clamps, graspers, scissors, staplers, and needle holders. The working tools are similar to those used in conventional (open) surgery, except that the working end of each tool is separated from its handle by an approximately 12-inch long extension tube. To perform surgical procedures the surgeon passes instruments through the cannulas and manipulates them inside the abdomen by sliding them in and out through the cannulas, rotating them in the cannulas, and "levering" (pivoting) them around centers of rotation approximately defined by the incisions in the muscles of the abdominal wall. The abdominal incisions do not provide stable reference positions or points of rotation, and so in order to maintain accurate positional control of an instrument during manipulation, the surgeon may need to manually constrain it to pivot around a fixed point coincident Faith the incision. Manual support of the pivot point is particularly important when the surgeon manipulates laparoscopes or other heavy instruments. Mechanical clamping devices are used to support the instruments in fixed orientations, but these devices do not provide a remote center of rotation for positioning the instruments.

In robotically assisted and telerobotic laparoscopic abdominal surgery the position of the surgical instruments is controlled by servo motors rather than directly by hand or with fixed clamps. With servo control, a means must be provided to ensure that the surgical instrument is constrained to move around a fixed center of rotation coincident with an entry incision in the patient's abdominal wall. Any other types of motion such as translation or rotation about other centers could cause patient injury.

Heretofore, there have been mechanisms directed to providing assistance in surgery. Thus, U.S. Pat. No. 4,756,655 to Jameson is directed to a manipulating mechanism having a control handle adapted to be positioned freely in three dimensions, a fixture for supporting a tool to be positioned, a linkage system which causes the end of the tool to move in the same direction as the control handle and a support structure. The linkage system includes a first linkage connected between the control handle and an effective ball-and-socket joint and a second linkage connected between the effective ball and socket joint and the fixture. Each linkage includes four link members rotatably connected in a parallelogram and a gimbal connected to one of the link members for mounting the linkage from the support structure.

The linkage system includes a first linkage connected between the control handle and a joint and a second linkage connected between the first linkage and the fixture. In the preferred embodiments, the linkage system is comprised of two motion translation mechanisms connected in series through an effective ball-and-socket joint, where each translation mechanism is essentially a pantograph adapted for rotation with respect to the support structure about two perpendicular axes. The motion of the control handle induces oppositely (or similarly, depending on the embodiment) directed motion of the ball-and-socket joint by means of one translation mechanism which in turn causes similarly directed motion of the tool by means of the second translation mechanism so that the motion of the tool is in the same direction as the motion of the control handle. The linkage system is directed to a master reflection system controlling a slave reflection mechanism and does not provide a remote center of spherical rotation.

U.S. Pat. No. 4,143,652 to Meier and Dbaly discloses a surgical retaining device for holding a surgical instrument in place, typically with hooks. The device includes a holder block for displaceably securing the surgical retaining device at a stationary object and at least one insert element into which there can be inserted and fixedly clamped the surgical instrument. Between the insert element and the holder block there is arranged a double-arm pivotable stand possessing an intermediate pin joint. The pivotable stand is connected at one end by means of a ball-and-socket joint at the insert element and at its other end by means of a further ball-and-socket joint with an overhang arm which can be fixedly clamped at random elevational and angular positions with respect to the holder block at the latter.

A paper given at the IEEE Engineering in Medicine and Biology Society 11th Annual International Conference in 1989 entitled SMOS: Stereotaxical Microtelemanipulator for Ocular Surgery shows a structure for use in ocular vitrectomy, and other medical fields such as radial keratotomy and plastic surgery. FIGS. 2 and 3 of the paper shows the mechanical structure of the SMOS. A carrier holds a rotatably mounted curved wrist. An instrument holder is movably mounted to the wrist for carrying an instrument or needle for working in the eye keeping the needle centered on the entrance aperture. This is described as realized in spherical coordinates in a reference whose zero point is the entrance aperture A. The mechanism creating these movements, which are in themselves the main actions of the vitrectomy operation, is called the wrist of the microtelemaninulator.

An article entitled "Robotic Surgery" in the March 1993 issue of IEEE Engineering in Medicine and Biology shows a motorized frame (FIG. 8) for use in prostate surgery. FIG. 8 shows a schematic layout of the main mechanical components of the device called SARP. The working envelope is small and can be flexibly constrained using mechanical stops to improve safety. The envelope is approximately the frustum of a cone. Several cones may be needed, depending on the size of the prostate, to remove the unwanted enlarged tissue from within the prostate.

The manual frame can only produce conical cavities because it is manually driven. However, the motorized frame is capable of producing both conical and barrel shape cavities. As a start, conical cavities are advocated to avoid moving along more than one axis at a time. Conical cavities are easy to produce using hot loop electrosurgery. Similar to the manual frame, a ring shape frame fitted with a diametrical arch is a carriage that carries the resectoscope. A C-shaped bracket fixed to the resectoscope helps ease the introduction of the motorized frame to the resectoscope. The axes are designed to be driven by motors. Back driving is possible when the servo action is disabled. Successive cuts are made by extending and retracting the cutting loop repeatedly and turning on the cutting current at the return stroke of the cutter. The ring moves to a new position for each cut. Several conical cavities can be resected from the prostate to relieve blockage. To achieve one or more of these conical cavities inside the prostate, the frame is fixed to a head travel so that it can move axially along the rotation axis of the ring axis.

None of the above-mentioned devices provide a light weight simple apparatus for providing a remote center of rotation for use in surgery with minimal obstruction of the surgical field as is disclosed and claimed herein.

SUMMARY OF THE INVENTION

In a broad aspect an apparatus is provided for moving an instrument about a spherical center of rotation at a desired location of the instrument. A base support means is adapted to be fixedly mounted to a surface. First linkage means are pivotally mounted on the base support means for rotation about an axis. Holding means are provided for holding an instrument in a position so that the desired remote center of spherical rotation of the instrument lies on the axis of rotation of the first linkage means. A second linkage means is connected to the holding means and pivotally connected to the first linkage means so that the remote center of spherical rotation of the instrument is maintained at the desired location.

The present invention provides a device for providing a remote center of spherical rotation for an instrument. A pivot joint having an x—x axis of rotation has a first linkage having one end pivotally mounted thereon. The axis of rotation of the first linkage is normal to and intersects the x—x axis. The other end is remote from the pivot joint. A parallelogram linkage is provided with a driving end and a remote end. The parallelogram linkage includes two sets of two corresponding members pivotally connected in a parallelogram. The parallelogram linkage is located in a plane parallel with the first linkage and has the driving end pivotally connected to the remote end of the first linkage. A mounting means for an instrument extends from the remote end of the parallelogram linkage. The mounting means is adapted to position the axis of the instrument held thereby to intersect the x—x axis to provide a center of spherical rotation for the instrument at a desired location.

In a more specific aspect the invention provides a device for providing a remote center of spherical rotation for an instrument for conducting laparoscopic surgery including a base support means adapted to be fixedly mounted to a surface and a pivot plate pivotally mounted to the base support means and having a rotational axis thereabout. At least a pair of linkage elements are extended from the pivot plate in parallel plane relationship. One end of the linkage elements is pivotally mounted in spaced apart relationship to the pivot plate. A parallelogram linkage means is connected to the linkage elements and includes two sets of two corresponding link members pivotally connected in a parallelogram, one of the sets of the two corresponding link members adapted to remain always parallel to the rotational axis, one of the link members of the set of corresponding link members adopted to remain always parallel to the rotational axis being pivotally connected to both linkage elements, one of the linkage elements being pivotally connected to both link members adopted to remain always parallel to the rotational axis. The parallelogram linkage means has an operating end and a driving end. An instrument element extends from the operating end of the parallelogram linkage means for movement therewith. The instrument element intersects the rotational axis at the location on the element desired for the remote center of rotation.

The remote center positioner is useful in a variety of applications. For example, supporting a microscope or other instrument to scan over and inspect a spherical surface. Various tools or instruments (manually or robotically positioned) that are passed through narrow entry ports can be supported by the apparatus of the present invention. Other uses include robotically-assisted positioning of an laparoscope for laparoscopic surgery, with the user commanding the position and orientation of the laparoscope via digital speech recognition, foot-switches, head-tracking or eye-tracking devices; support of manually-positioned laparoscopes or other surgical instruments during laparoscopic surgery; and telerobotic manipulation of laparoscopic surgical instruments (laparoscopes and various working tools) in which the positions of the working end of the tools are under servo control, and follow the motions of a surgeon's hands as he manipulates input control devices at a location that may be remote from the patient. Position, force, and tactile feedback sensors may be employed to transmit position, force, and tactile sensations from the working tool tips back to the surgeon's hands as he operates the telerobotic system.

OBJECTS OF THE INVENTION

A particular object of the present invention is to provide apparatus useful to support an instrument or the like and includes the ability to move the instrument to perform a variety of tasks while maintaining a center of spherical rotation at a desired location of the instrument. Additional objects and advantages of the present invention will become apparent from the description of the various embodiments thereof read in light of the attached drawings which are made part of this specification.

BRIEF DESCRIPTION OF THE DRAWINGS

FIG. 2 is an elevation view of the preferred embodiment of a remote center positioner;

FIG. 2a is an enlarged sectional view taken at section a—a of FIG. 2;

FIG. 3 is an end view of the preferred embodiment of the remote center position of FIG. 2;

FIG. 6 is an elevation view illustrating a manual application of the remote center positioner in accordance with the present invention;

FIG. 8 is an elevation view of another embodiment of apparatus of the invention; and FIG. 8a is a sectional view taken at line a—a of FIG. 8.

DESCRIPTION OF THE INVENTION

Figure 1:
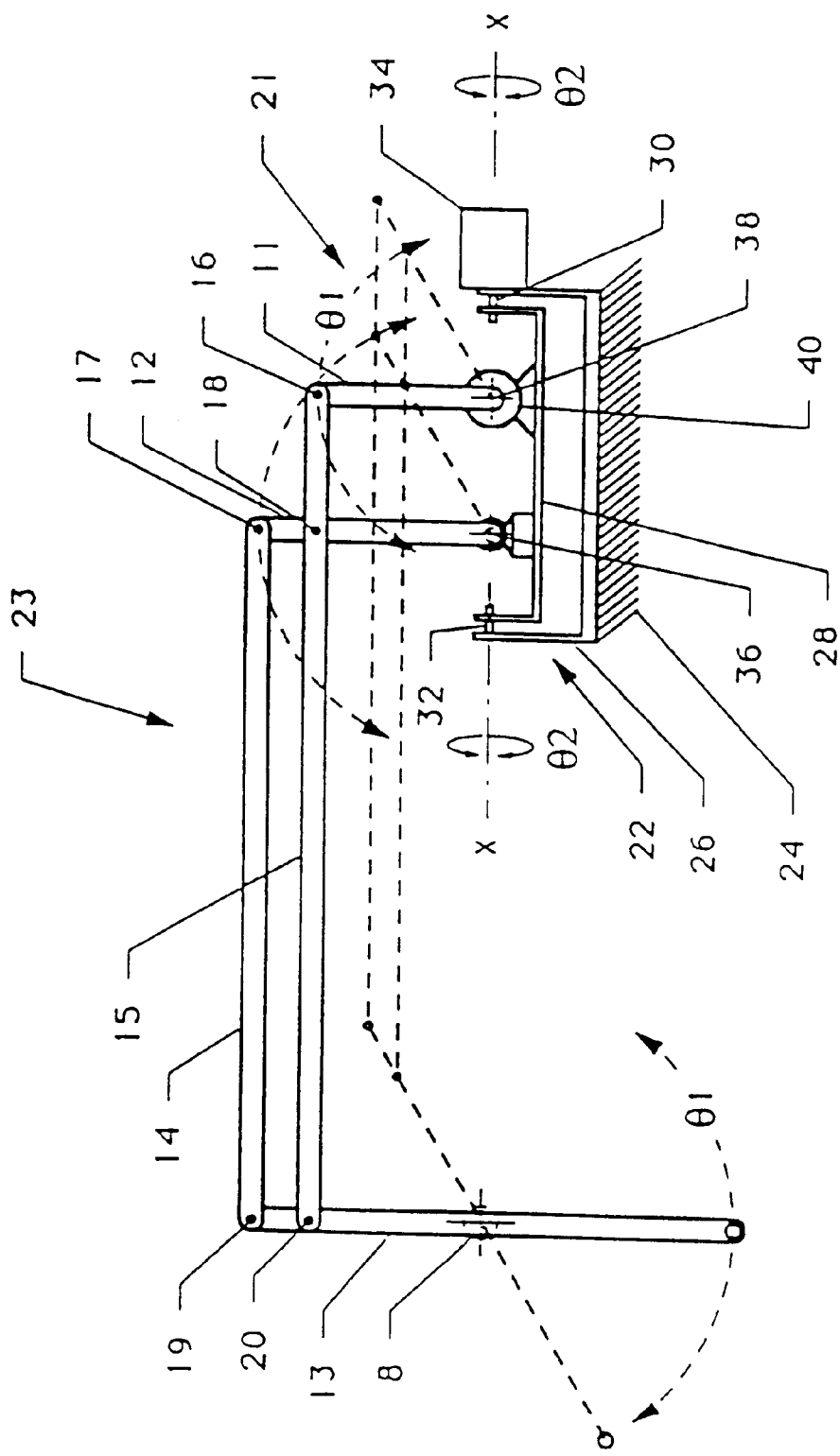
FIG. 1 is a elevation view of an embodiment of a remote center positioner.

FIG. 1 is an elevation view of an embodiment of a remote center positioner in a basic form in accordance with the present invention. A first linkage means is indicated generally by the numeral 21 and a second linkage in the form of a parallelogram is indicated by the numeral 23. The first linkage means is pivotally mounted on a base plate for rotation about an x—x axis. The second linkage means is pivotally connected to the first linkage means and is adapted to move in a plane parallel to the first linkage. Five link members (including extensions thereof), 11, 12, 13, 14, and 15 are connected together with pivot joints 16–20. A portion of element 13 extends beyond pivot 20 of the parallelogram linkage. The parallelogram linkage has an operating end at link member 13 and a driving end at link member 12. The elongated element 13 may, as desired later, carry a surgical instrument or other device. The pivot joints allow relative motion of the link members only in the plane containing them.

A parallelogram linkage is formed by corresponding link members 14, 15 and link members 12 and 13. The portions of link members 14 and 15 of the parallelogram are of equal length as are the portions of members 12 and 13 of the parallelogram. These members are connected together in a parallelogram for relative movement only in the plane formed by the members. A rotatable joint generally indicated by the numeral 22 is connected to a suitable base 24. The rotatable joint 22 is mounted on a base plate 26 adapted to be fixedly mounted to the base support means 24. A pivot plate 28 is pivotally mounted to base plate 26 by suitable means at, such as, pivots 30, 32. Thus pivot plate 28 may be rotated about axis x—x through a desired angle θ2. This may be accomplished manually or by a suitable pivot drive motor 34.

A first linkage is pivotally mounted on the pivot plate 28 of the rotatable joint 22. The linkage elements 11, 12 and the link members are relatively stiff or inflexible so that they may adequately support an instrument used in surgical operations. Rods made of aluminum or other metal are useful as such links. The linkage elements 11 and 12 are pivotally mounted on base plate 28 for rotation with respect to the rotatable joint by pivots 36 and 38. At least one of the pivots 36, 38 is positioned so that its axis of rotation is normal to and intersects the x—x axis. Movement nay occur manually or may occur using a linkage drive motor 40. The first linkage is also shaped in the form of a parallelogram formed by linkage elements 11, and 12; the portion of link member 15 connected thereto by pivots 16, 18; and base plate 28. One of the link members 15 is thus utilized in both the first 21 and second 23 linkage means. Linkage element 12 also forms a common link of both the first linkage means 21 and the second linkage means 23. In accordance with the invention, a remote center of spherical rotation 8 is provided by the above described embodiment of apparatus when the linkage element 11 is rotated and/or when pivot plate 28 is rotated about axis x—x. Thus the end of element 13 can be moved through desired angles θ1 and θ2 or rotated about its own axis while the remote center of rotation remains at the same location.

The preferred embodiment of apparatus assembled in accordance with the present invention is illustrated in FIGS. 2, 2a and 3. FIG. 2 is an elevation view, FIG. 2a is an enlarged sectional view taken at a—a of FIG. 2 and FIG. 3 is an end view of the remote positioning apparatus. Many of the elements of the preferred embodiment are the equivalent to elements of the FIG. 1 embodiment. These elements will be designated with the same numbers primed in FIGS. 2 and 3. Thus a pivot plate 28' is rotatably mounted on a base support means 26' by suitable means such as pivots 30', 32'. The pivot plate and the base plate form a rotatable joint 22' which has a rotation axis designated as x—x. The base plate may be fixedly mounted to a suitable base support means 24'.

Two linkage elements 11' and 12' extend from the pivot plate 28'. Mounting means 36' and 38' are provided to pivotally mount one end of each of the linkage elements to the pivot plate. The axis of rotation of the linkage elements are normal to and intersecting the x—x axis. A channel shaped link member 115 is pivotally connected by suitable pivot joints 16' and 18' to the other ends of linkage elements 11', 12' (respectively) equidistant from pivot plate 28'. A corresponding link member 15' is located internally of link member 115 and is pivotally connected to the upper end of linkage element 12'. A link member 13' corresponding in length to the link member 12' between pivots 17', 18' is pivotally connected to link member 15' at pivot 19' and to link member 115 at pivot 20'. An instrument mounting means 44 is fixedly mounted to link member 13' for movement therewith. The axis of an instrument held in the instrument mounting means 44 intersects the x—x axis of the rotating joint 22'. Thus an instrument held in the mounting means would have a remote center of spherical rotation about the position indicated by the numeral 8' in FIG. 2.

A drive motor 434 incorporating a shaft-angle position sensor is operably connected to the pivot plate 28'. A second drive motor 440 incorporating a shaft-angle position sensor is operably connected to linkage element 11'. Suitable motor drive and control circuits may be connected to motor/sensor 440 and motor/sensor 434 via power and sensor cables 436 and 435 (respectively) to operate the present apparatus under open-loop or closed-loop servo control. The details of the mounting arrangement for the instrument mounting means are shown in FIG. 2a which is a sectional view taken at a—a of FIG. 2. As there shown the mounting means 44 is fixedly connected via multiple-axis force and torque sensor 400 and pin member 118 to link member 13' for movement therewith. Link member 13' is pivotally connected at pivot 20' to the channel shaped link member 115 by bearing means 116, 117 formed about pin member 118. Link member 15' is pivotally connected to link member 13' at 19' by means of bearing means 120 and pin member 121.

A suitable sensor interface circuit may be connected to the force and torque sensor 400 via cable 401 so that sensor signals arising from forces and torques applied to an instrument supported in the mounting means 44 can be detected and used for monitoring or controlling operation of the present apparatus. For example, the sensor signals can be used as feedback signals in master-slave force-reflecting telerobotic servo control of the invention such that the input control device responds only to forces exerted on the supported instrument and is not affected by inertial loads, gravity forces, or external forces acting on linkage elements other than mounting means 44.

An apparatus is provided for moving an instrument about a spherical center of rotation at a desired location of the instrument. A base support means is adapted to be fixedly mounted to a surface. First linkage means 11', 12' are pivotally mounted on the base plate for rotation about an axis. A holding means 44 is provided for holding an instrument in a position so that the desired remote center of spherical rotation of the instrument intersects the axis and a second linkage means 15', 115 and 13' is connected to the holding means and pivotally connected to the first linkage means by pivots 17', 18', 16' whereby the remote center of spherical rotation of the instrument is maintained at the desired location.

Figure 4:
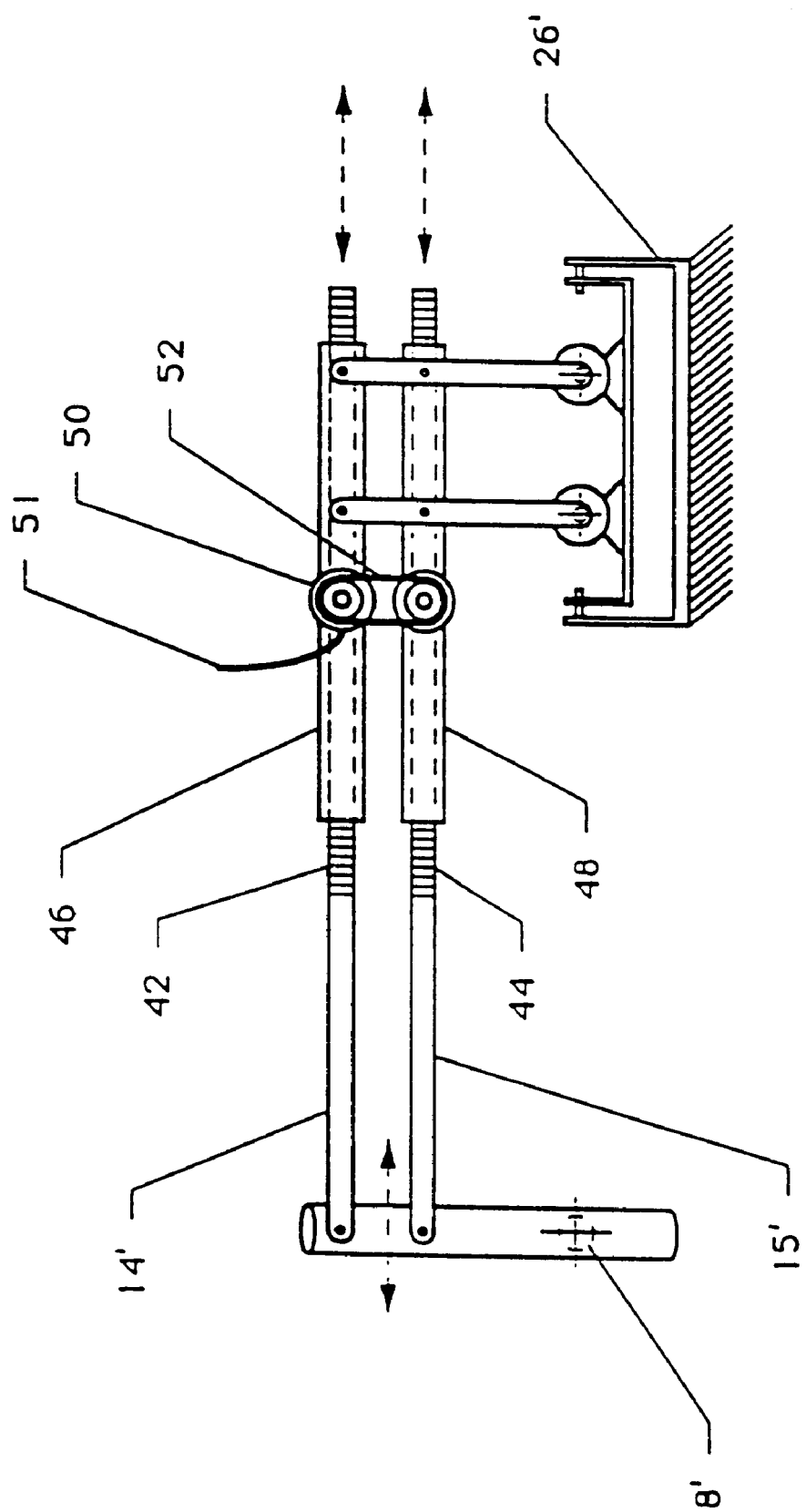
FIG. 4 is a elevation view illustrating an embodiment of the remote center positioner in accordance with the invention having an adjustable center distance.

FIG. 4 is a schematic elevation view of another embodiment of apparatus assembled in accordance with the present invention. In many instances it may be desirable to have a means of adjusting the remote center of rotation 8' relative to the mounted position of base plate 26'. Thus it would be desirable to axially extend or retract the horizontal members 14', 15' of the parallelogram linkage. The length of the two corresponding members 14', 15' must be increased or decreased in equal amounts to maintain the parallelogram geometry of the linkage.

The axial length adjustment could be provided in many ways. For example, as shown in FIG. 4, a portion of members 14', 15' are provided with racks 42, 44. Tubular members 46, 48 enclose members 14', 15'. The members 14', 15' are extended or retracted by suitable means such as drive motor 50, motor lead 51 and drive belt 52. Other means for axially extending or retracting the members are available. For example, coupled lead screws could be used or the members could be manually fixed into the desired position in the tubular members using ratchets, pins or spring detents.

Figure 5:
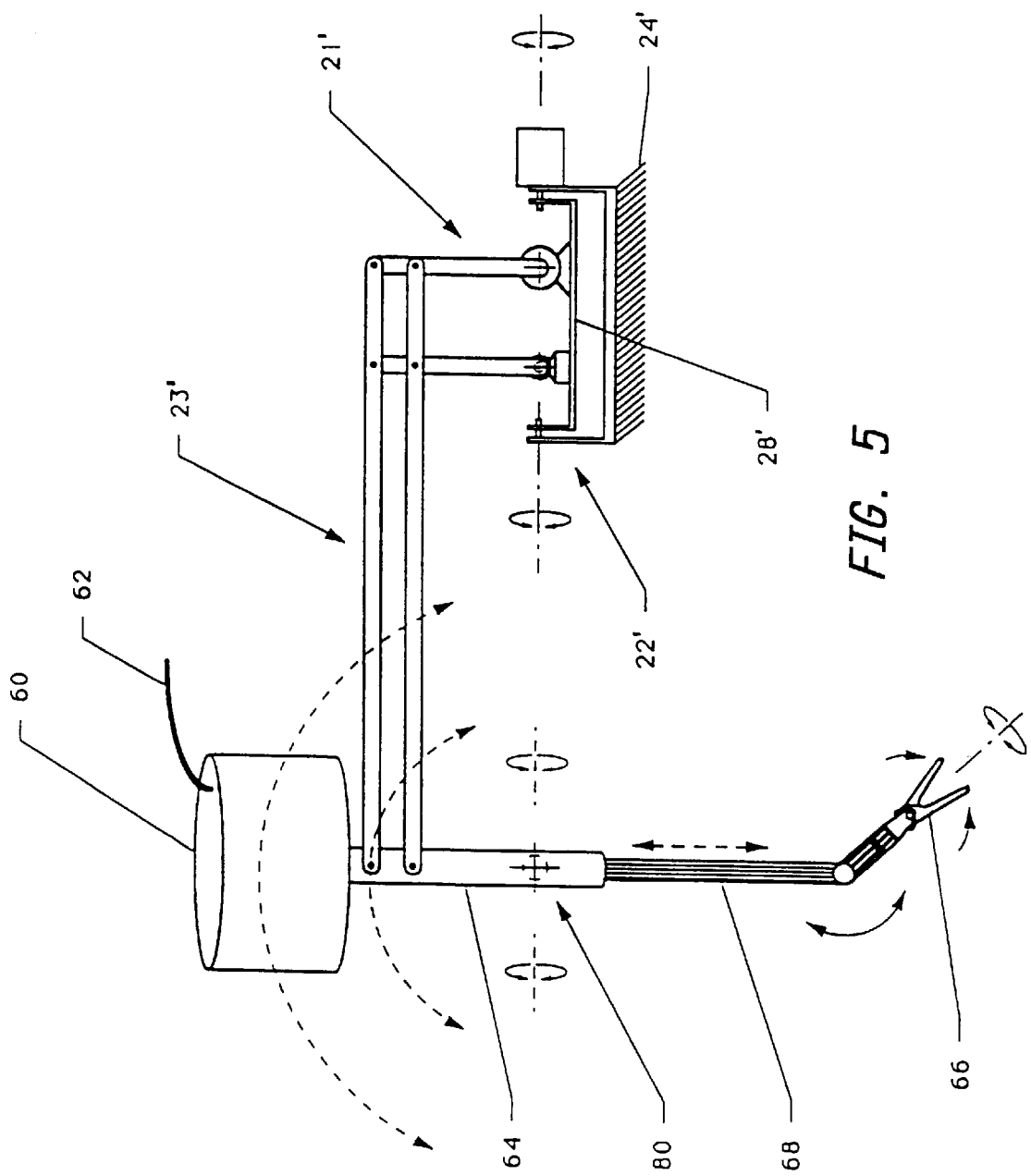
FIG. 5 is an elevation view illustrating a motor driven application of the remote center positioner in accordance with the present invention.

FIG. 5 illustrates an embodiment of apparatus assembled in accordance with the invention wherein a motor driven arrangement is positioned on the operating end of the parallelogram linkage. A drive unit 60 is connected by power and control cable 62 to a source of power and control and a cannula 64 is provided which may be passed through a patient's abdominal wall. An instrument 66 is attached to an operating element 68 and may be manipulated as indicated in FIG. 5. The remote center positioners as described heretofore will maintain the center of spherical rotation at position 80 while the instrument 66 is being manipulated.

FIG. 6 is an elevation view illustrating a manual application of the remote center positioner of the present invention. A handle 71 for operating a surgical instrument 73 is connected to the operating end of the remote center positioner. Movement of the cannula 75 will be constrained to rotation about the center 80' of spherical rotation.

Figures 7, 7A:
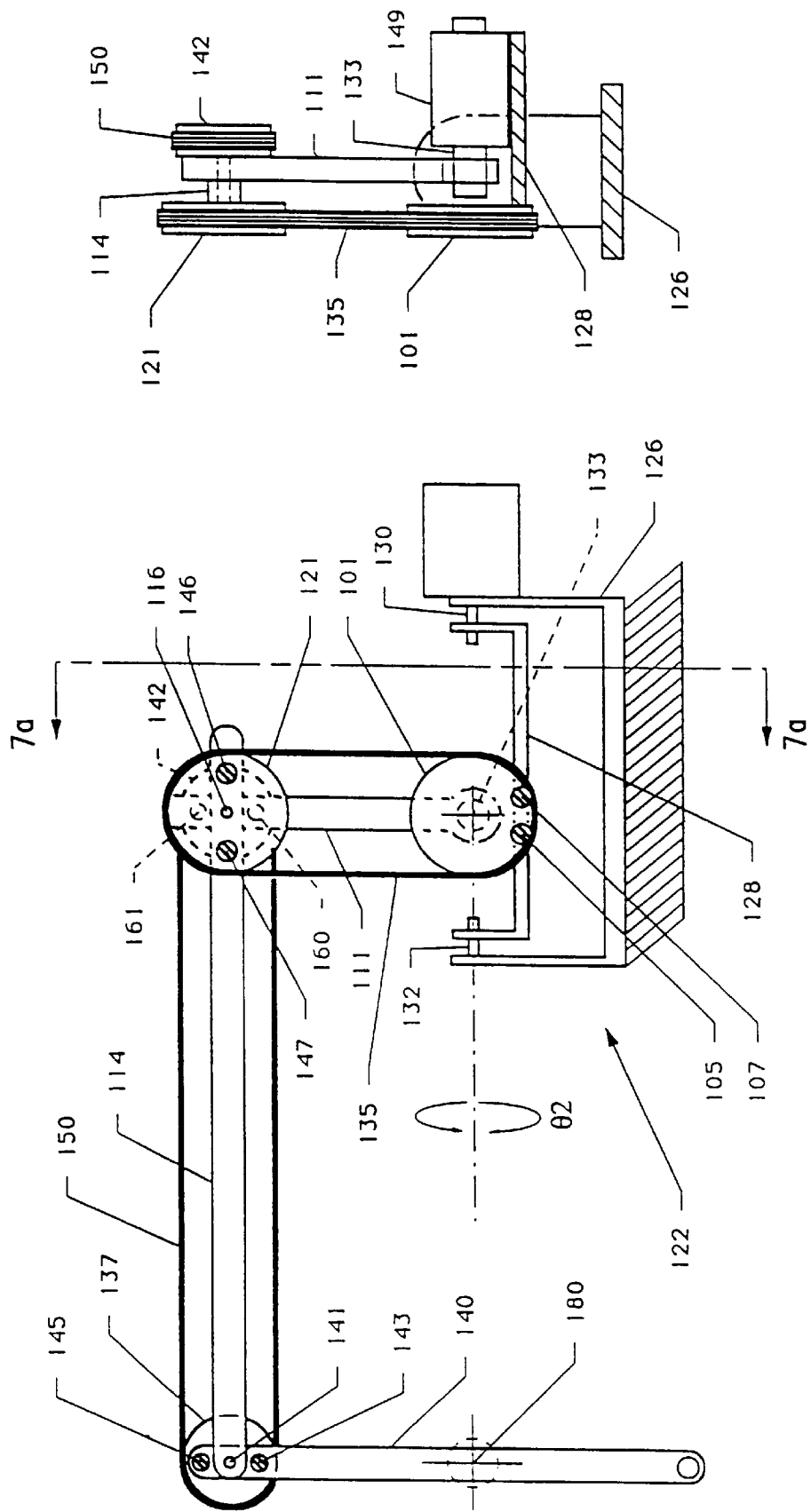
FIG. 7 is an elevation view of another embodiment of apparatus of the invention.
FIG. 7a is a sectional view taken at line a—a of FIG. 7.

FIG. 7 is an elevation view and FIG. 7a is a sectional view taken at a—a of FIG. 7 of an embodiment of the invention which utilizes a flexible drive element in the linkage of the remote center positioner. A rotatable joint is indicated by the numeral 122. The rotatable joint rotates about an x—x axis. Thus pivot plate 128 can be rotated about pivots 130, 132 through a desired angle θ2 with respect to base plate 126. A linkage element 111 is pivotally mounted on the pivot plate by pivot 133. The pivot 133 is positioned so that its axis of rotation is normal to and intersects the x—x axis. A pulley 101 is positioned to be coaxial with the axis of rotation of the pivot 133. It is evident that the term pulley can include wheels, sprockets or the like. The pulley is fixedly connected to the base plate 128 by suitable means such as screws 105, 107. Thus the pulley will not rotate with respect to the base plate 128.

A link member 114 is pivotally connected by pivot joint 116 to linkage element 111. A second pulley 121 coaxial with pivot 116 is fixedly connected to link member 114 by screws 146 and 147. A flexible drive link 135 such as a belt, chain, or a cable is connected around the pulleys 121, 101 in a non slip mode (such as a bicycle chain or timing belt). Pulleys 121 and 101 are of equal diameter as are pulleys 142 and 137. A link member 140 is pivotally connected to the operating end of link member 114 by means of pivot joint 141.

A third pulley 137 coaxial with pivot 141 is fixedly connected to link member 140 by means of screws 143, 145. A fourth pulley 142 coaxial with pivot 116 is fixedly connected to link element 111 by screws 160 and 161. A second flexible drive link 150 is connected around pulleys 137 and 142 in non slip relationship. Thus when linkage element 111 is rotated about pivot 133 by linkage drive motor 149 for example, the motion is transmitted by the pulleys to link member 140 which is constrained to move in parallel relationship with element 111. In this manner a remote center of rotation is maintained as indicated by 180 in FIG. 7.

FIG. 8 is an elevation view and FIG. 8a is a sectional view taken at a—a of FIG. 8 of another embodiment of the present invention.

A rotatable joint is shown and is indicated generally by the number 222. The rotatable joint rotates about a x—x axis. Thus pivot plate 228 can be rotated around pivots 230, 232 through a desired angle θ2. A linkage element 211 is pivotally mounted on the pivot plate 228 by pivot 233. The axis of the pivot 233 is located normal to and intersecting the x—x axis of rotation. A pulley 201 is positioned to be coaxial with the axis of rotation of the pivot 233. The pulley is fixedly connected to the base plate by suitable means such as screws 205, 207.

A pair of link members 214, 215 are pivotally connected to linkage element 211 by pivots 212 and 216 respectively. The other end of the link members 214 and 215 are pivotally connected to an instrument holding means or the like indicated by 240 by suitable pivot joints 241, 242. A second pulley 231 is fixedly connected to link element 215 by suitable screws 251, 252. The pulley 231 is mounted coaxially with the axis of rotation of the pivot joint 216. A flexible drive link 260 is connected around both pulleys 201 and 231 in non slip relationship. The effect of this construction constrains link members 215 and 214 to remain parallel with the x—x axis during movement and also constrains element 240 to remain parallel with linkage element 211 during movement, thus causing the center of spherical rotation of the instrument or the like to remain at point 280.

The principles, preferred embodiments and modes of operation of the present invention have been described in the foregoing specification. However, the invention which is intended to be protected is not to be construed as limited to the particular embodiments disclosed. The embodiments are to be construed as illustrative rather than restrictive. Variations and changes may be made by others without departing from the spirit of the present invention. Accordingly, all such variations and changes which fall within the spirit and scope of the present invention as defined in the following claims are expressly intended to be embraced thereby.

What is claimed is:

1. A surgical manipulator for moving an instrument about a desired spherical center of rotation at a desired fixed location along the instrument, the manipulator comprising:

a base support adapted to be fixedly mounted to a surface;

a first linkage, including at least a first rod, pivotally mounted on the base support for rotation about a first axis;

an instrument holder having a longitudinal second axis wherein the instrument is held parallel to the second axis, such that the desired remote center of spherical rotation of the instrument is at the intersection of the first and second axes;

a second linkage having a proximal end and a distal end, including at least a second rod, the proximal end of the second linkage being pivotally connected to the first linkage and the distal end of the second linkage being pivotally connected to the instrument holder for moving the instrument holder in a parallel plane relationship to the first linkage such that the spherical center of rotation is maintained at the desired fixed location; and an instrument drive unit coupled to the instrument holder, the instrument drive unit controlling movement of the instrument relative to the spherical center of rotation, the instrument drive unit comprising a linear actuator for reciprocating the instrument in a direction parallel to the second axis;

the instrument drive unit further comprising a first drive coupled to the instrument holder, the first drive having an actuator for rotating the instrument about the second axis, said instrument having an end effector for interacting with a surgical site;

wherein the instrument drive unit further comprises a second drive coupled to the instrument holder for actuating the end effector about a third axis.

2. A surgical manipulator system comprising:

a surgical instrument having a longitudinal instrument axis, the instrument further comprising a shaft having proximal and distal ends and an end effector coupled to the distal end, wherein the end effector is movably coupled to the distal end of the shaft at a pivot;

an instrument holder for positioning the instrument in a direction so the instrument axis intersects a desired point;

a base;

a first linkage, including at least a first rod having a proximal end and a distal end, wherein the proximal end of the first linkage is mounted to the base;

a second linkage, including at least a second rod pivotally connected to the distal end of the first linkage, the second linkage being pivotally connected to the instrument holder such that the first linkage and second linkage can rotate the instrument about the desired point; and an instrument drive unit mounted on the second linkage and coupled to the surgical instrument, the instrument drive unit manipulating the instrument relative to the desired point, wherein the instrument drive unit comprises a linear actuator for reciprocating the instrument along the instrument axis and a first drive coupled to the instrument holder, the drive having an actuator for rotating the instrument about the instrument axis, and wherein the instrument drive unit further comprises a second drive coupled to the instrument holder for actuating the end effector.

3. A surgical manipulator system comprising:

a base support adapted to a fixedly mounted to a surface;

a surgical instrument having an elongate shaft with a proximal end and a distal end, an instrument axis therebetween, and an end effector movably coupled to the distal end at a pivot;

a first linkage, including at least a first rod having a proximal end and a distal end, wherein the proximal end of the first linkage is mounted to the base support;

a second linkage, including at least a second rod pivotally connected to the distal end of the first linkage, the second linkage pivotally supporting the instrument such that the first linkage and second linkage can position the end effector about a desired center of rotation; and an instrument drive unit mounted on the second linkage near the surgical instrument, the drive unit having a linear actuator for reciprocating the instrument in a direction parallel to the instrument axis, a first drive for rotating the instrument about the instrument axis, and a second drive for rotating the end effector about the pivot.

4. The system of claim 3 further comprising an instrument holder, the instrument holder positioning the instrument along the instrument axis so that the desired center of rotation is fixed along the instrument axis.

5. The system of claim 3, wherein the desired center of rotation is an insertion point.

6. The system of claim 3, wherein the desired center of rotation is movable.

7. A robotic surgical apparatus for delivering an endoscopic surgical instrument to a surgical site in a patient comprising:

an articulate arm assembly having a plurality of linkages and joints and a distal portion; and an elongate tubular structure having a longitudinal aperture therethrough, said tubular structure coupled to said distal portion of said articulate arm assembly, said tubular structure adapted to be inserted through an aperture in a body wall of said patient, wherein said longitudinal aperture of said tubular structure is able to slidably engage an elongate shaft of an endoscopic surgical instrument having an end effector.

8. The apparatus of claim 7, wherein said tubular structure is used to guide said instrument through said body aperture so that the end effector is positioned adjacent the surgical site.

9. The apparatus of claim 7, wherein said tubular structure is removably connected to said articulate arm assembly.

10. The apparatus of claim 7, wherein said instrument is secured to said articulate arm assembly by engagement with said longitudinal aperture of said cylindrical structure.

11. The apparatus of claim 7 or 10, wherein said instrument is engaged by said longitudinal aperture in such a manner that a remotely-operated drive assembly can move the end effector of said instrument to manipulate tissue at the surgical site.

12. The apparatus of claim 11, wherein said drive assembly comprises an actuator for rotating the instrument about an instrument longitudinal axis.

13. The apparatus of claim 11, wherein said drive assembly comprises a servomechanism coupled to an input control device for remotely controlling movement of the surgical instrument.

14. The apparatus of claim 11 further comprising a sensor coupled to the drive assembly for detecting forces or torques applied to the instrument by the drive assembly.

15. The apparatus of claim 14, wherein said drive assembly comprises a servomechanism operatively coupled to an input control device for remotely controlling movement of the surgical instrument according to an operator's input; and a feed back control assembly operatively coupled to the sensor and the servomechanism for transmitting signals representative of the forces or torques applied to the instrument to the input control device for sensing by an operator.

16. The apparatus of claim 7, wherein said instrument comprises said end effector coupled to a wrist member coupled to said elongate shaft, wherein said end effector can move relative to said elongate shaft in at least two degrees of freedom.

17. The apparatus of claim 16, wherein said elongate shaft has a longitudinal axis, wherein said at least said two degrees of freedom comprise actuation of the end effector and rotation of the end effector about a distal axis angularly disposed to the longitudinal axis of said elongate shaft.

18. The apparatus of claim 17, wherein said distal axis is substantially perpendicular to said longitudinal axis.

19. The apparatus of claim 7 or 16, wherein a drive assembly maneuvers said instrument in at least two degrees of proximal freedom of movement around a center of motion coincident with a longitudinal axis of said elongate shaft, said center of motion further substantially in the vicinity of said body aperture.

20. The apparatus of claim 19, wherein said plurality of linkages and joints comprise a parallelogram system useful for supporting the tubular structure and for retaining said center of motion on said longitudinal axis.

21. The apparatus of claim 7, wherein said elongate shaft has a distal end, wherein said end effector is movably coupled to the distal end of the elongate shaft at a pivot.

22. A method of delivering an endoscopic surgical instrument to a surgical site in a patient comprising:

providing an articulate arm assembly having a plurality of linkages and joints and a distal portion, said articulate arm assembly having an elongate tubular structure coupled to said distal portion, said tubular structure having a proximal end, a distal end, and a longitudinal aperture extending between said proximal and distal ends;

inserting said tubular structure into a body aperture; and slidably engaging an elongate shaft of an endoscopic surgical instrument through said tubular structure longitudinal aperture so that said instrument extends through said body aperture distal of said distal end of said tubular structure; and positioning an end effector of said instrument adjacent said surgical site.

23. The method of claim 22, wherein said tubular structure is inserted into the body aperture after the instrument is slidably engaged in the longitudinal aperture of said tubular structure.

24. The method of claim 22, further comprising controlling movement of said end effector to manipulate tissue at the surgical site.

25. The method of claim 24, further comprising rotating the instrument about an instrument longitudinal axis.

26. The method of claim 22, wherein said instrument comprises said end effector coupled to a wrist member coupled to said elongate shaft, wherein said method further comprises controlling movement of said end effector in at least two degrees of freedom relative to said elongate shaft.

27. The method of claim 24 or 26, wherein said controlling movement of the end effector comprises manipulating an input device remote from the surgical site, said input device operatively connected to the articulate arm assembly and the instrument so that movement of the instrument corresponds to how an operator moves the input device.

28. The method of claim 22 or 26, said method further comprising maneuvering said surgical instrument in at least two degrees of proximal freedom of movement around a center of motion coincident with a longitudinal axis of said elongate shaft and with said body aperture.

29. The method of claim 28, wherein said plurality of linkages and joints comprise a parallelogram system useful for supporting the tubular structure and for retaining said center of motion on said longitudinal axis.

30. The method of claim 26, wherein said elongate shaft has a longitudinal axis, wherein said at least said two degrees of freedom comprise actuation of the end effector and rotation of the end effector about a distal axis angularly disposed to the longitudinal axis of said elongate shaft.

31. The method of claim 30, wherein said distal axis is substantially perpendicular to said longitudinal axis.

32. The method of claim 22, wherein said elongate shaft has a distal end, wherein said end effector is movably coupled to the distal end of the elongate shaft at a pivot, said method further comprising moving the end effector relative to the elongate shaft around said pivot and actuating the end effector to interact with tissue at the surgical site.

\* \* \* \* \*

UNITED STATES PATENT AND TRADEMARK OFFICE
CERTIFICATE OF CORRECTION

| | | |
|---|---|---|
| PATENT NO. | : 6,106,511 | Page 1 of 1 |
| DATED | : August 22, 2000 | |
| INVENTOR(S) | : Jensen, Joel F. | |

It is certified that error appears in the above-identified patent and that said Letters Patent is hereby corrected as shown below:

Column 1,
Line 11, please add

-- This invention was made with Government support under contract awarded by the National Institute for Health (NIH) under grant number 5R01GM-44902-02. The Government has certain rights in this invention. --

Signed and Sealed this

Eleventh Day of December, 2001

*Attest:*

NICHOLAS P. GODICI
*Attesting Officer*     *Acting Director of the United States Patent and Trademark Office*